United States Patent [19]

Fels et al.

[11] Patent Number: 4,980,171

[45] Date of Patent: Dec. 25, 1990

[54] PHARMACEUTICAL COMPOSITION FOR ORAL ADMINISTRATION, BASED ON A DIPHOSPHONIC ACID DERIVATIVE

[75] Inventors: Jean-Pierre Fels, Castelnau le lez; Jean-Claude Gromenil, Montbazin-Poussan; Bernard Abramovici, Juvignac, all of France

[73] Assignee: Societe Anonyme dite : SANOFI, Paris, France

[21] Appl. No.: 333,966

[22] Filed: Apr. 6, 1989

[30] Foreign Application Priority Data

Apr. 7, 1988 [FR] France .................................. 88 04628

[51] Int. Cl.$^5$ ................................................ A61K 9/74
[52] U.S. Cl. ..................... 424/473; 424/451; 424/464; 424/465; 424/452
[58] Field of Search ............... 424/451, 464, 489, 452, 424/465, 473

[56] References Cited

U.S. PATENT DOCUMENTS

| | | | |
|---|---|---|---|
| 3,962,432 | 6/1976 | Schmidt-Dunker | 554/108 |
| 4,054,598 | 10/1977 | Blum et al. | 562/13 |
| 4,064,164 | 12/1977 | Blum et al. | 562/13 |
| 4,330,530 | 5/1982 | Baker | 514/825 |
| 4,613,496 | 9/1986 | Kopf et al. | 424/451 |

FOREIGN PATENT DOCUMENTS

| | | |
|---|---|---|
| 2259615 | 6/1975 | France . |
| 2319645 | 3/1977 | France . |
| 2319646 | 3/1977 | France . |
| 2135879 | 8/1984 | United Kingdom . |

*Primary Examiner*—Merrell C. Cashion, Jr.
*Assistant Examiner*—Leon R. Horne
*Attorney, Agent, or Firm*—Bacon & Thomas

[57] ABSTRACT

The invention relates to oral pharmaceutical compositions comprising a diphosphonic acid derivative and sodium laurylsulfate in the amount of 1.5 to 6% by weight, relative to the diphosphonic compound.

4 Claims, No Drawings

PHARMACEUTICAL COMPOSITION FOR ORAL ADMINISTRATION, BASED ON A DIPHOSPHONIC ACID DERIVATIVE

The present invention relates to a pharmaceutical composition for oral administration, based on a diphosphonic acid derivative and containing an appropriate amount of sodium laurylsulfate. Such a pharmaceutical composition has an excellent bioavailability in human.

In the description and in the claims which follow, diphosphonic acid derivative is understood as meaning a compound of the formula

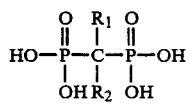  (I)

in which $R_1$ represents a hydrogen atom, a halogen atom, a hydroxyl, an amino or a dialkyl($C_1$-$C_4$)amino, and $R_2$ represents a halogen atom, a linear alkyl containing from 1 to 5 carbon atoms which is unsubstituted or substituted by a chlorine atom, a hydroxyl, an amino or a dialkyl($C_1$-$C_4$)amino, or $R_2$ represents a phenoxy, a phenyl, a thiol, a phenylthio, a chlorophenylthio, a pyridyl or a thiomorpholin-4-yl, and their salts with pharmaceutically acceptable mineral or organic acids.

These compounds are known. They have been described as drugs which are useful in the oral treatment of bone complaints or articular complaints of the arthritis type, especially in the following patents: BE No. 902308, BE No. 865434, EP No. 203649, DE No. 2130794, BE No. 822930, U.S. Pat. No. 4,134,969, EP No. 162510, FR No. 2525223, EP No. 39033, U.S. Pat. No. 4,578,376, U.S. Pat. No. 4,621,077, JP No. 55-98193, EP No. 186405, EP No. 100718, WO No. 86/00902, WO No. 87/03598 and FR No. 2531088.

The following compounds may be mentioned in particular as diphosphonic acid derivatives:

1-hydroxyethylidenediphosphonic acid, whose international common name is etidronic acid, and its sodium salts;

2-(pyridin-2-yl)ethylidenediphosphonic acid, whose international common name is piridronic acid, and its sodium salts;

dichloromethylenediphosphonic acid, whose international common name is clodronic acid, and its sodium salts;

3-amino-1-hydroxypropylidenediphosphonic acid, whose international common name is pamidronic acid, and its sodium salts;

4-amino-1-hydroxybutylidenediphosphonic acid and its salts;

6-amino-1-hydroxyhexylidenediphosphonic acid and its salts;

phenoxymethylenediphosphonic acid and its salts;

thiomorpholinomethylenediphosphonic acid and its salts; and 4-chlorophenylthiomethylenediphosphonic acid, called compound A below, and its pharmaceutically acceptable salts, especially the disodium salt of compound A.

Compound A and its salts are described in French patent No. 2 531 088. These compounds have antirheumatic and antiarthritic properties and they also inhibit bone resorption. These compounds can be used in the treatment of rheumatoid polyarthritis, Paget's disease and osteoporosis.

It is known that diphosphonic acid derivatives are useful as drugs in the oral treatment of bone complaints or articular complaints of the arthritis type. It is also known that these derivatives are not well absorbed when they are administered orally and that, to overcome this poor absorption, it is necessary to administer high dosages of active principle.

U.S. Pat. No. 4,230,700 describes a method of treating Paget's disease which comprises concurrently administering a diphosphonate and an antirachitic vitamin D. It is stated in the specification of the said patent (page 9 lines 6 to 10 and lines 49–50) that:

the oral mode of administration is the preferred mode;

high dosages of the active principle are required because of the limited oral absorption of the active principle (the diphosphonate); and the absorption of high dosages of active principle produces toxic effects and must be avoided.

Example 1 of the said patent describes a capsule having the following composition:

| | |
|---|---|
| diodium salt of 1-hydroxy-ethylidenediphosphonic acid | 350 mg |
| vitamin $D_3$ | 3000 IU |
| starch | 55.60 mg |
| sodium laurylsulfate | 2.90 mg |

In this Example, the amount of sodium laurylsulfate contained in the capsule is about 0.8% by weight relative to the disodium salt of 1-hydroxyethylidenediphosphonic acid and about 1% by weight relative to the free acid.

European patent application No. 88 462 describes a pharmaceutical composition comprising a pharmacologically active and effective amount of an organophosphonate and a pharmacologically active and effective amount of a steroid, it also being possible for the said composition to contain additional constituents, conventionally used in pharmaceutical compositions, in customary proportions. Sodium laurylsulfate is mentioned among these possible additional constituents.

The said document indicates that, on oral administration, only 10% of the organophosphonate is absorbed by the intestine, the remainder being excreted.

It has now been found that if sodium laurylsulfate is added to the diphosphonic acid derivative, in an oral pharmaceutical composition, in an amount greater than or equal to 1.5% by weight relative to the diphosphonic derivative, the absorption of the said diphosphonic derivative is improved.

It has also been found, surprisingly, that this improved absorption results in an increase in the amount of product absorbed without giving absorption peaks capable of having a toxic effect.

It has been found, totally surprisingly, that the best absorption of the diphosphonic acid derivative is accompanied by a very distinct decrease in the absorption variations between individuals and hence by a more homogeneous response of the treated population towards the dosage of diphosphonic acid derivative administered.

Finally, it has been found that this improved bioavailability enables sufficient and uniform blood levels to be achieved with smaller dosages of diphosphonic acid derivative than the doses normally employed in therapy.

This property is all the more surprising if one considers that, in the two documents cited above, sodium laurylsulfate is specifically mentioned, but either in insufficient proportions to give an absorption-potentiating effect, as in the case of U.S. Pat. No. 4,230,700, or generically as a surface-active excipient, as in the case of European patent application No. 88 462.

Thus the present invention relates to a pharmaceutical composition based on a diphosphonic acid derivative I or a pharmaceutically acceptable salt, which comprises from 1.5 to 6% by weight of sodium laurylsulfate relative to the diphosphonic acid derivative.

According to the present invention, the preferred pharmaceutical compositions are those containing a diphosphonic acid derivative selected from etidronic acid, piridronic acid, pamidronic acid, clodronic acid, 4-chlorophenylthiomethylenediphosphonic acid, 4-amino-1-hydroxybutylidenediphosphonic acid, 6-amino-1-hydroxyhexylidenediphosphonic acid, phenoxymethylenediphosphonic acid, thiomorpholinomethylenediphosphonic acid or one of their pharmaceutically acceptable salts.

Such a composition has an improved bioavailability in human compared with a composition not comprising sodium laurylsulfate.

In particular, such a pharmaceutical composition contains compound A or its disodium salt as the active principle.

Preferably, the pharmaceutical composition comprises between 100 mg and 500 mg of 4-chlorophenylthiomethylenediphosphonic acid (compound A) or the equivalent amount of its disodium salt, and the amount of sodium laurylsulfate is between 1.7 and 4% by weight relative to the diphosphonic acid derivative.

The pharmaceutical composition according to the invention can be in the form of tablets, capsules, powder, granules or drops or in any other form which can be administered orally. The tablet form is a preferred form.

The composition according to the invention can also contain ingredients customarily used in pharmacy for the preparation of oral forms. Thus the composition according to the invention may contain a disintegrating agent, a flowing agent, a lubricant and any suitable bulking excipient.

Lactose, cellulose or starches can be used as the bulking excipient. Stearic acid, magnesium stearate, L-leucine or, for example, glycerol tribehenate can be used as the lubricant. Sodium carboxymethyl starch, crosslinked sodium carboxymethyl cellulose or, for example, crosslinked polyvinylpyrrolidone can be used as the disintegrating agent. Pure silica or colloidal silicon dioxide can be used as the flowing agent.

The present invention further relates to instantaneously dissolving oral forms and to effervescent oral forms obtained by adding an effervescent pair of compounds to the composition according to the invention. Examples of effervescent pairs of compounds which can be used are tartaric acid and sodium bicarbonate or citric acid and sodium bicarbonate.

The tablet form is a preferred form according to the invention. The invention further relates to instantaneously dissolving tablets, effervescent tablets and coated tablets.

The pharmaceutical compositions are described as Examples and in no way limit the scope of the invention.

EXAMPLE 1

Divisible tablet:

| | |
|---|---|
| disodium salt of compound A, corresponding to 200 mg of compound A | 240 mg |
| sodium laurlsulfate | 4.5 mg |
| crosslinked sodium carboxymethyl cellulose | 24 mg |
| microcrystalline lactose | 177 mg |
| magnesium stearate | 4.5 mg |
| | 450 mg |

EXAMPLE 2

Divisible tablet:

| | |
|---|---|
| disodium salt of compound A, corresponding to 200 mg of compound A | 240 mg |
| sodium laurylsulfate | 8 mg |
| crosslinked sodium carboxymethyl cellulose | 24 mg |
| microcrystalline lactose | 173.5 mg |
| magnesium stearate | 4.5 mg |
| | 450 mg |

A study of bioavailability in human was carried out with the tablets prepared according to Examples 1 and 2.

This study was carried out on healthy volunteers by comparing the results obtained after oral administration of the composition according to Example 1 of the invention with the results obtained after oral administration of a capsule or a sachet containing the same amount of active principle, corresponding to 200 mg of compound A, but not containing sodium laurylsulfate.

The capsule contains the active principle and an appropriate excipient. The sachet contains the active principle only.

PROTOCOL OF THE CLINICAL TRIAL

Twelve healthy volunteers of the male sex, aged between 20 and 28 years, took part in the trial. None of the subjects had a particular medical history. The clinical and laboratory examinations were normal. None of the subjects had received drugs during the 2 weeks prior to the trial, or absorbed calcium-rich food within the 48 hours immediately preceding the trial.

After overnight fasting, the 3 formulations (tablet, capsule, sachet) were absorbed with 150 ml of mineral water with a low calcium content (1.55 mg).

The trial consists of 3 administrations separated by intervals of one week. For each of the administrations, the dose corresponding to 400 mg of compound A is given in the form of 2 capsules, 2 tablets or 2 sachets in a single administration.

The order in which the formulations were administered, corresponding to 6 different sequences, was as follows:

| Subject no. | Order of administration | | |
|---|---|---|---|
| | 1 | 2 | 3 |
| 1, 2 | tablet | capsule | sachet |
| 3, 4 | tablet | sachet | capsule |
| 5, 6 | capsule | tablet | sachet |
| 7, 8 | capsule | sachet | tablet |
| 9, 10 | sachet | tablet | capsule |
| 11, 12 | sachet | capsule | tablet |

8 ml blood samples were taken at the following times: before treatment and then 0.5, 1.0, 1.5, 2.0, 2.5, 3.0, 4.0, 6.0, 8.0, 10.0, 12.0, 24.0, 36.0 and 48.0 hours after administration of the pharmaceutical composition. The unchanged active principle was determined in these different samples.

ANALYSIS OF THE SAMPLES

Compound A was determined by high performance liquid chromatography with UV detection.

The selectivity, exactness and reproducibility of the method were checked. The limit of quantification is about 0.05 mg/l.

A calibration curve was established every day and control samples were included in all the individual kinetics.

PHARMACOKINETIC INTERPRETATION

The following pharmacokinetic parameters were determined from the plasma concentrations of compound A:
Cmax: maximum plasma concentration observed,
Tmax: time required to reach the value Cmax,
AUC: area under the curve of plasma concentrations, calculated by the trapezium method between the times 0 and 48 h.

To facilitate comparisons between the different trials, the maximum plasma concentrations and the areas under the curve were standardized for a body weight of 70 kg by applying the following correction factor:

$$\text{standardized parameter} = \text{measured parameter} \times \frac{\text{individual weight (kg)}}{70}$$

PHARMACOKINETIC PARAMETERS

Examination of the plasma profiles for each subject shows a very large scatter of the results for some of the subjects in the case of the sachet and capsule forms. These differences are evident to a lesser extent in the case of the tablet form, although they do not totally disappear. The Cmax and AUC values show a smaller variability for the tablet form (coefficient of variation of the order of 30% for the tablet form and greater than 60% for the capsule and sachet forms). The results are collated in Table 1 below.

TABLE 1

Mean pharmacokinetic parameters obtained after a single administration of 400 mg of active principle in the form of 2 tablets, 2 capsules or 2 sachets

| Parameter | Tablet | Capsule | Sachet |
|---|---|---|---|
| Tmax (h) | 1.25 | 3.15 | 3.13 |
| (± SD) | (0.40) | (0.87) | (1.03) |
| Cmax* (mg/l) | 3.00 | 1.06 | 0.97 |
| (± SD) | (0.98) | (0.92) | (0.62) |
| AUC 0–48 h* (mg.h/l) | 30.91 | 11.94 | 12.48 |

TABLE 1-continued

Mean pharmacokinetic parameters obtained after a single administration of 400 mg of active principle in the form of 2 tablets, 2 capsules or 2 sachets

| Parameter | Tablet | Capsule | Sachet |
|---|---|---|---|
| (± SD) | (9.79) | (7.63) | (7.75) |

The standard deviations (± SD) are indicated for each value.
*Parameter standardized for a body weight of 70 kg.

The times taken to reach the plasma concentration peak (Tmax) are significantly shorter with the tablet than with the capsule and the sachet (1.25±0.40 h for the tablet, 3.15±0.87 h for the capsule and 3.13±1.03 h for the sachet). The difference between sachet and capsule is not statistically significant.

The tablet produces distinctly higher maximum plasma concentrations (Cmax) with very highly significant differences compared with both the capsule and the sachet (3.00±0.98 mg/l for the tablet, 1.06±0.92 mg/l for the capsule and 0.97±0.62 mg/l for the sachet). The difference between sachet and capsule is not statistically significant.

Comparison of the areas under the plasma concentration curve (AUC) at 48 hours for the 3 forms studied shows that the mean bioavailability of the tablet according to the invention is 3 times greater than that of the other two forms. The differences between the areas under the curves are very highly significant between the tablet and the sachet or between the tablet and the capsule. By contrast, no significant difference is noted between the capsule and the sachet.

The study of bioavailability in human was repeated under the same conditions with tablets prepared according to Example 2.

The results obtained are collated below:

| Tmax | 1.56 h (± 1.02) |
|---|---|
| Cmax* | 2.46 mg/l (± 0.98) |
| AUC* 0–48 hours | 23.94 mg.h/l (± 5.21) |

The standard deviations (± SD) are indicated.
*Parameter standardized for a body weight of 70 kg.

These results are comparable to those obtained with the tablets prepared according to Example 1.

CONCLUSION OF THE STUDY

The pharmaceutical composition according to the invention makes it possible to obtain:
a more rapid absorption of compound A,
a bioavailability which is about 3 times greater than that of the other two forms, and
a reduced variability between individuals in terms of the plasma concentrations.

No signs of poor tolerance were observed after administration of the pharmaceutical composition according to the invention.

What is claimed is:

1. A pharmaceutical composition for oral administration, based on a diphosphonic acid derivative of the formula

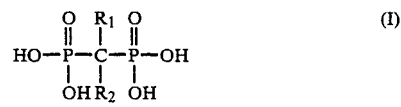

in which $R_1$ represents a hydrogen atom, a halogen atom, a hydroxyl, an amino or a dialkyl($C_1$-$C_4$)amino, and $R_2$ represents a halogen atom, a linear alkyl containing from 1 to 5 carbon atoms which is unsubstituted or substituted by a chlorine atom, a hydroxyl, an amino or a dialkyl($C_1$-$C_4$)amino, or $R_2$ represents a phenoxy, a phenyl, a thiol, a phenylthio, a chlorophenylthio, a pyridyl or a thiomorpholin-4-yl, or one of its pharmaceutically acceptable salts, which comprises from 1.5 to 6% by weight of sodium laurylsulfate relative to the diphosphonic acid derivative.

2. A pharmaceutical composition according to claim 1, wherein the diphosphonic acid derivative is selected from etidronic acid, piridronic acid, clodronic acid, pamidronic acid, 4-chlorophenylthiomethylenediphosphonic acid, 4-amino-1-hydroxybutylidenediphosphonic acid, 6-amino-1-hydroxyhexylidenediphosphonic acid, phenoxymethylenediphosphonic acid, thiomorpholinomethylenediphosphonic acid or one of their pharmaceutically acceptable salts.

3. A pharmaceutical composition according to claim 1, in which the diphosphonic acid derivative is 4-chlorophenylthiomethylenediphosphonic acid or its disodium salt.

4. A pharmaceutical composition according to claim 1, comprising from 100 to 500 mg of 4-chlorophenylthiomethylenediphosphonic acid or the equivalent amount of its disodium salt, and from 1.7 to 4% by weight of sodium laurylsulfate.

* * * * *